United States Patent [19]
Hahn

[11] Patent Number: 5,305,766
[45] Date of Patent: Apr. 26, 1994

[54] NEEDLE CAP WRENCH AND METHOD

[76] Inventor: James K. Hahn, 900 N. Poplar, Newton, Kans. 67114

[21] Appl. No.: 973,422

[22] Filed: Nov. 9, 1992

[51] Int. Cl.$^5$ ............................................. A47F 13/06
[52] U.S. Cl. ...................................... 604/192; 128/919
[58] Field of Search ............ 604/187, 110, 192, 263, 604/197, 198; 128/919; 206/364–366; 234/1.1, 2, 10

[56] References Cited

U.S. PATENT DOCUMENTS

| | | | |
|---|---|---|---|
| 3,329,146 | 7/1967 | Waldman | 604/192 |
| 4,485,918 | 12/1984 | Meyer | 206/366 |
| 4,596,562 | 6/1986 | Vernon | 604/192 |
| 4,717,386 | 1/1988 | Simmons | 604/192 |
| 4,921,199 | 5/1990 | Villaveces | 248/314 |
| 4,938,514 | 7/1990 | D'Addezio | 294/16 |
| 4,986,817 | 1/1991 | Code | 604/192 |
| 5,000,742 | 3/1991 | Morrison | 604/192 |
| 5,002,536 | 3/1991 | Thompson et al. | 604/192 |
| 5,021,049 | 6/1991 | Howard | 604/192 |
| 5,112,314 | 5/1992 | Aragon et al. | 604/192 |
| 5,125,912 | 6/1992 | Kinnel | 604/263 |
| 5,156,426 | 10/1992 | Graves | 294/1.1 |
| 5,183,469 | 2/1993 | Capaccio | 604/192 |
| 5,190,169 | 3/1993 | Sincock | 211/60.1 |

Primary Examiner—Jerome L. Krutner
Attorney, Agent, or Firm—John W. Carpenter

[57] ABSTRACT

A tool wrench for removing and replacing a needle cap from a combined needle cap and needle assembly. The tool or wrench has a generally longitudinal wrench structure defining a generally cylindrical opening having a cylindrical wall with at least one arcuate channel traversing the cylindrical wall. A method for removing a needle cap from a needle assembly that is releasably engaged to a syringe.

8 Claims, 9 Drawing Sheets

NEEDLE CAP WRENCH AND METHOD

BACKGROUND OF THE INVENTION

1. Field of the Invention

This invention pertains to a tool and method for safely releasing, removing, and replacing a needle cap, or a combined needle cap and needle assembly from a hypodermic syringe or similar injection device.

2. Description of the Prior Art

A patentability investigation was conducted and the following U.S. Patents by Nos. were discovered: U.S. Pat. No. 4,596,562 to Vernon; U.S. Pat. No. 4,717,386 to Simmons; U.S. Pat. No. 4,938,514 to D'Addezio; U.S. Pat. No. 5,061,248 to Sacco; U.S. Pat. No. 5,078,696 to Nedbaluk; and U.S. Pat. No. 5,112,314 to Aragon et al.

SUMMARY OF THE INVENTION

The tool or wrench of this invention is a one piece needle cap decapping/recapping and needle removal and ejection device comprised of a thin, flat, member provided with one or more hole or holes, each customized or configured to accommodate generally a needle cap or needle assembly of a particular configuration or design. It is designed to permit the operator to safely decap and recap an injection device or needle assembly, remove the needle assembly from the syringe, and eject the same into an appropriate container thereby permitting the operator to fully comply with the OSHA requirement for safe needle handling.

The present invention accomplishes its desired objects by broadly providing a tool or wrench for removing and replacing a needle cap from a combined needle cap and needle assembly comprising a generally longitudinal wrench structure defining a generally cylindrical opening having a cylindrical wall with at least one arcuate channel traversing the cylindrical wall. The cylindrical wall has a pair of first opposed arcuate channels traversing the cylindrical wall, and a pair of second opposed arcuate channels.

The distance between one of the first opposed arcuate channels and one of the second opposed arcuate channels is defined by an approximate 90 degree arc. Stated alternatively, the first and the second arcuate channels are generally equispaced from each other along the cylindrical wall. The generally longitudinal structure of the tool or wrench further defines a first recess and a second recess terminating in a first wrench platform and a second wrench platform respectively. The tool or wrench is formed with a first ridge integrally formed on the first wrench platform and circumscribing the generally cylindrical opening, and a second ridge integrally formed on the second wrench platform and also circumscribing the generally cylindrical opening which opens on both the first wrench platform and the second wrench platform. The longitudinal wrench structure additionally defines a first continuous perimetrical ridge integrally secured to the first wrench platform and forming boundaries for the first recess, and a second continuous perimetrical ridge integrally secured to the second wrench platform and forming boundaries for the second recess. A needle cap is slidably engaged to the generally longitudinal wrench structure through the generally cylindrical opening. The needle cap has a structure generally defining a longitudinal hollow cup-like structure having at least one external rib slidably disposed in the at least one arcuate channel within the generally cylindrical opening. A hypodermic needle is slidably disposed in the needle cap, and a generally hollow top is slidably engaged to the needle cap for encapsulating the hypodermic needle within the needle cap.

The present invention further accomplishes its desired objects by further broadly providing a method for removing a needle cap from a needle assembly that is engaged to a syringe comprising the steps of:

(a) providing a tool comprising a generally longitudinal wrench structure defining a generally cylindrical opening having a cylindrical wall with at least one arcuate channel traversing the cylindrical wall;

(b) providing a needle cap having a structure generally defining a longitudinal hollow cup-like structure having at least one external rib, with the needle cap being releasably engaged to a needle assembly that is releasably engaged to a syringe;

(c) passing the needle cap through the cylindrical wall opening of the tool such that the at least one external rib is slidably disposed in the at least one arcuate channel of the cylindrical wall opening; and (d) moving the tool such that the needle cap is released and removed from the needle assembly.

The moving step (d) additionally comprises removing the needle assembly from the syringe such that the needle cap and the needle assembly are removed from the syringe. The method additionally comprises covering the needle assembly with a needle assembly cap; and the covering comprises slidably engaging the needle cap with the needle assembly cap such as to encapsulate the needle assembly. The method further additionally comprises disposing the needle cap, having the needle assembly cap slidably engaged thereto for encapsulating the needle assembly, in a generally upright vertical posture with the tool or wrench being slidably engaged to the needle cap. The needle cap may be removed from the tool or wrench while the needle assembly cap remains slidably engaged to the needle cap with the needle assembly being encapsulated within and between the combined needle cap and needle assembly cap.

It is therefore an object of the present invention to provide a tool or needle cap wrench for removing and replacing a needle cap from a combined needle cap and needle assembly.

It is another object of the present invention to provide a method for removing a needle cap from a needle assembly that is engaged to a syringe.

These, together with the various ancillary objects and features which will become apparent to those skilled in the art as the following description proceeds, are attained by this novel apparatus and method for removing a needle cap, a preferred embodiment as shown with reference to the accompanying drawings, by way of example only, wherein;

DETAILED DESCRIPTION OF THE INVENTION

Figure 1:
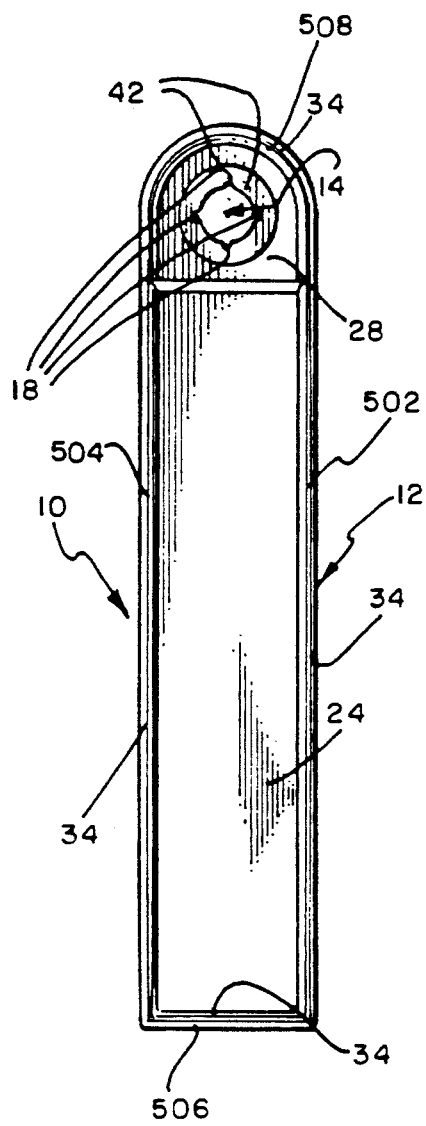
FIG. 1 is a top plan view of the wrench or tool of the present invention.
Figure 2:
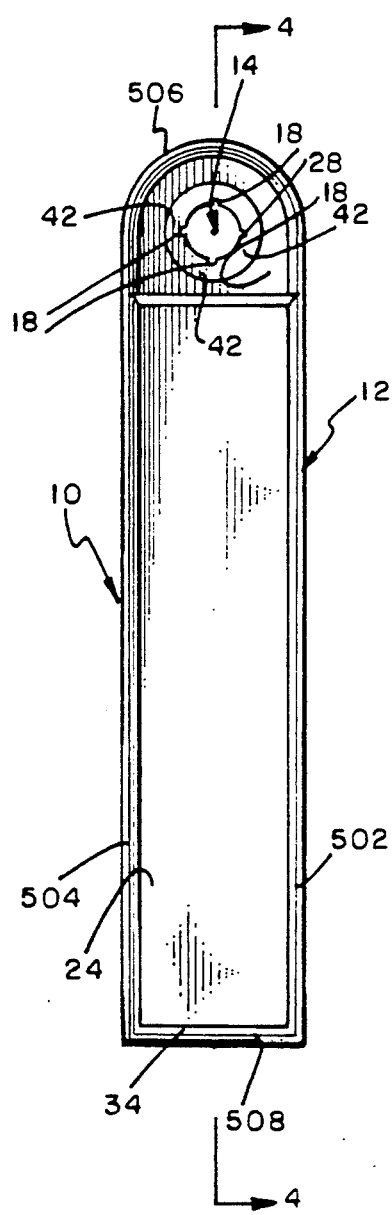
FIG. 2 is another top plan view of the wrench or tool of the present invention.
Figure 3:
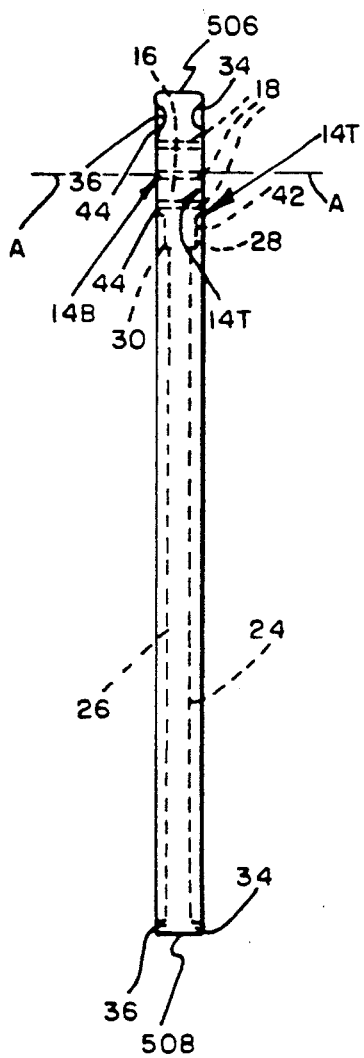
FIG. 3 is a side elevational view of the wrench or tool of the present invention.
Figure 4:
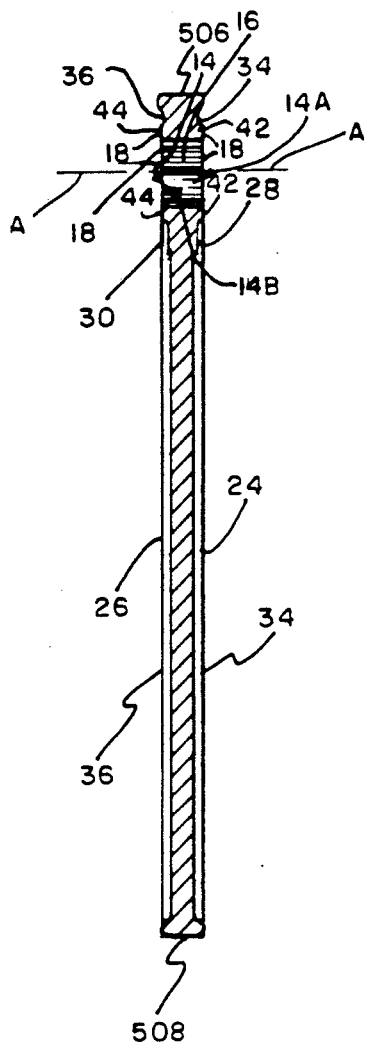
FIG. 4 is a vertical sectional view taken in direction of the arrows and along the plane of line 4—4 in FIG. 2.
Figure 5:
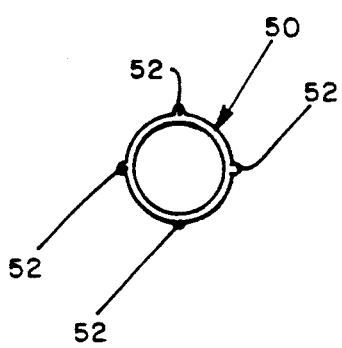
FIG. 5 is a horizontal sectional view of the removable cap which is to be engaged by the tool or wrench of the present invention.

Referring in detail now to the drawings, wherein similar parts of the invention are identified by like reference numerals, there is seen a tool or needle cap wrench, generally illustrated as 10. The wrench 10 broadly comprises a generally longitudinal wrench structure 12 having a generally cylindrical opening 14 having a cylindrical wall 16 with at least one arcuate (preferably semi-circular) channel 18. In a preferred embodiment of the invention, the cylindrical wall 16 is formed with four arcuate or semi-circular channels 18, all generally equispaced from each other along and/or in the cylindrical wall 16. Stated alternatively, the distance (i.e. arcuate distance) between any two contiguous channels 18 is defined by an approximately 90 degrees arc. The generally longitudinal wrench structure 12 has a pair of longitudinal recesses 24 and 26 disposed on opposite planar sides of the wrench structure 12, both terminating at one end in platforms 28 and 30 respectively. The other end of the recesses 24 and 26 in the wrench structure 12 terminate respectively in perimetrical ridges 34 and 36. The perimetrical ridge 34 is a continuous perimetrical ridge 34 integrally secured to the platform 28 and delineating and forming the boundaries for the recess 24. Similarly, perimetrical ridge 36 is a continuous perimetrical ridge 36 integrally secured to the platform 30 delineating and forming the boundaries for the recess 26. Also integrally formed with and/or secured to the platform 28 is a ridge 42 which elevates above platform 28 to a height that generally collimates or aligns with the height of the ridge 34 as best shown in FIGS. 3 and 4. Stated alternatively, a plane along the ridge 42 and a plane along the ridge 34 would be a common plane. Ridge 42 circumscribes or surrounds the generally cylindrical opening 14. Similarly, also integrally formed with and/or secured to the platform 30 is a ridge 44 which elevates above platform 30 to a height that generally collimates or aligns with the height of the ridge 36 as also best shown in FIGS. 3 and 4. Stated alternatively, a plane along the ridge 44 and a plane along the ridge 36 would be a common plane. Ridge 44 also circumscribes or surrounds the generally cylindrical opening 14.

Figure 17:
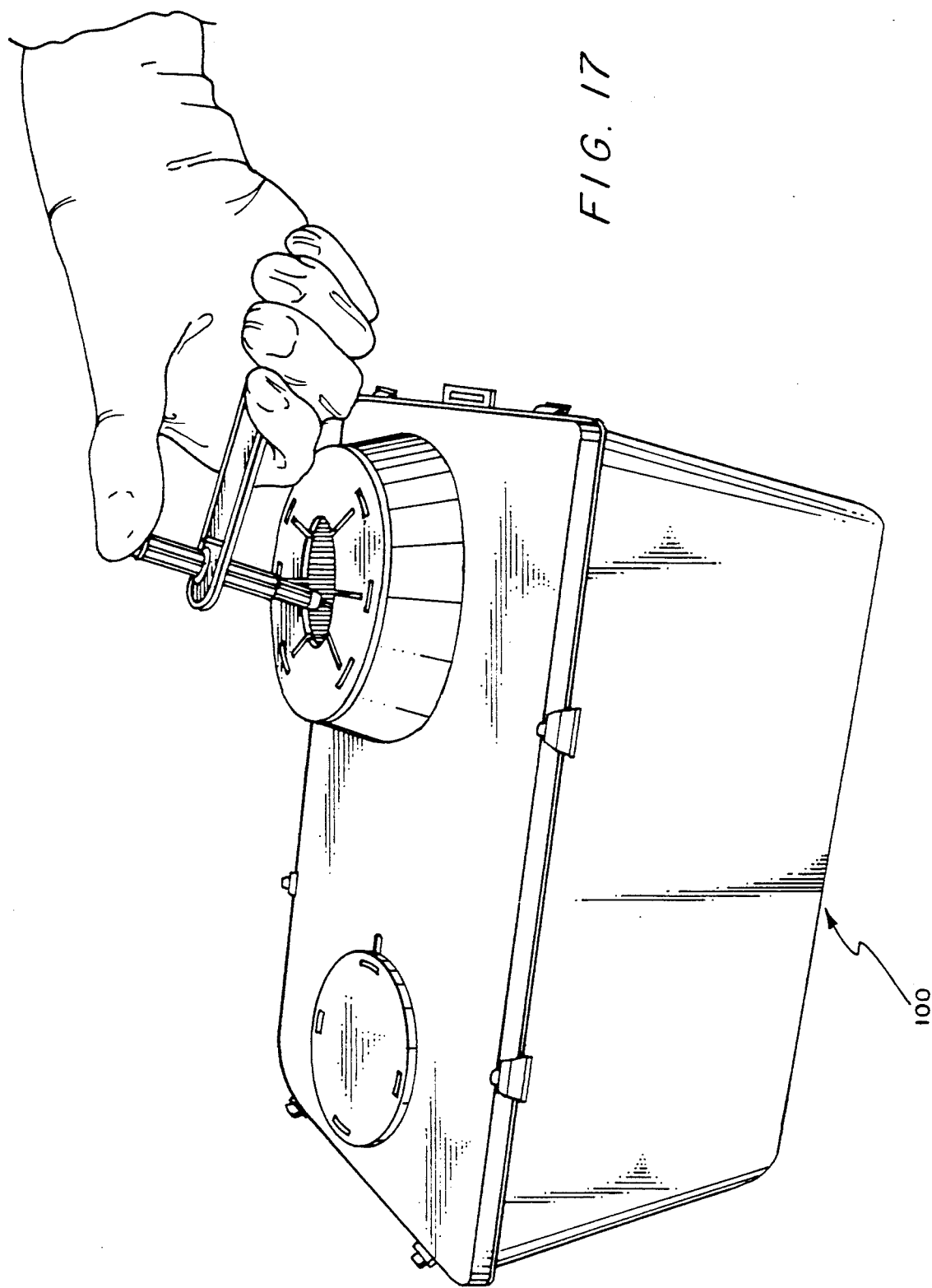
FIG. 17 is a perspective view of a combined needle cap and contaminated needle assembly in the process of being disposed in a container for receiving contaminated needles.

The generally cylindrical opening 14 is for engaging a needle cap, generally illustrated as 50. The needle cap 50 is for covering a needle assembly, generally illustrated as 60, that is removably engaged (more specifically, threadably secured) to a syringe, generally illustrated as 70. As will be further explained below, the tool or needle cap wrench 10 of this invention is for removing needle cap 50 off of the needle assembly 60 and for recapping the needle assembly 60 with the needle cap 50 all to protect the user from being stuck with a contaminated needle assembly 60. As will also be further shown below, the tool or needle cap wrench 10 of this invention is for also removing the needle assembly 60 from the syringe 70 simultaneously with removing the needle cap 50, all again to protect the user from being stuck with a contaminated needle assembly 60. After removal of the combined needle cap 50 and needle assembly 60 (which is slidably lodged in the needle cap 50), the needle assembly 60 may be covered with an assembly cap, generally illustrated as 80, which slidably engages the needle cap 50 to encapsulate the needle assembly 60. The combined needle cap 50/needle assembly 60 may be subsequently removed from the needle cap wrench 10 by downward pressure on the needle cap 50 (as best shown in FIG. 17) for disposing of the combined needle cap 50/needle assembly 60 through an aperture 102 in a suitable container 100. Alternatively, the combined needle cap 50/needle assembly 60/assembly cap 80 may be passed through aperture 102 and disposed in the container 100.

Figure 6:
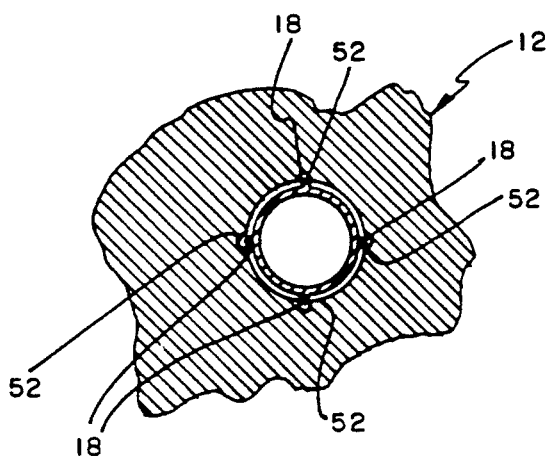
FIG. 6 is a partial horizontal sectional view of the wrench engaging the cap.
Figure 7:
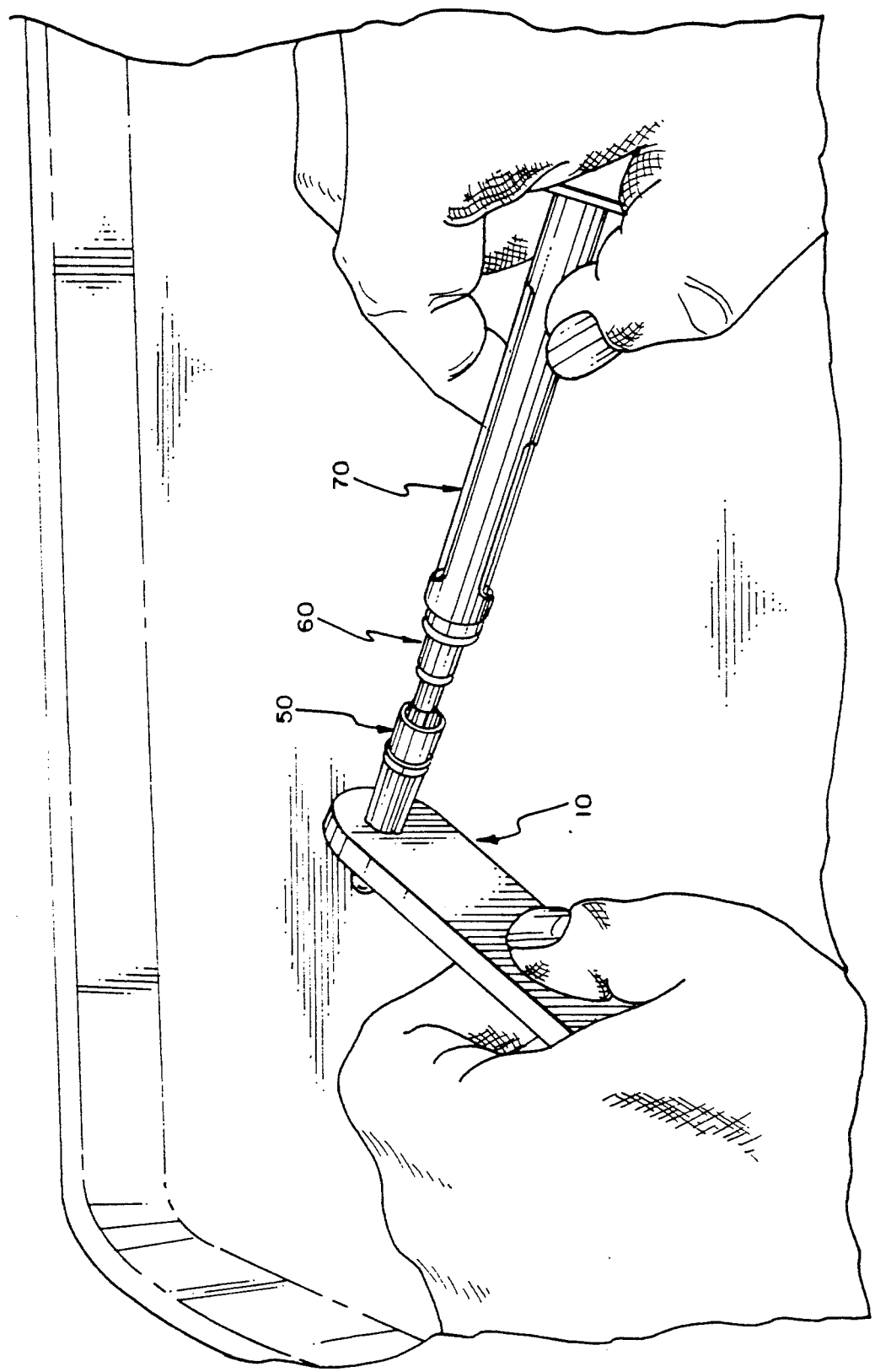
FIG. 7 is a perspective view of the wrench or tool engaged to the cap and being removed from a needle assembly having a syringe secured thereto.
Figure 18:
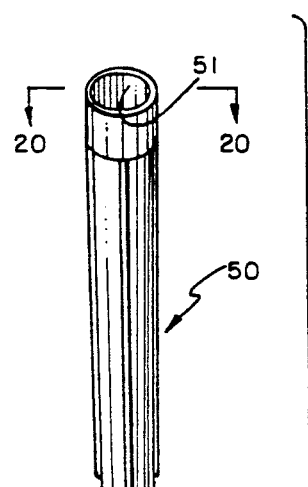
FIG. 18 is segmented partial perspective view of the needle assembly, the needle cap, and the wrench.
Figure 18:
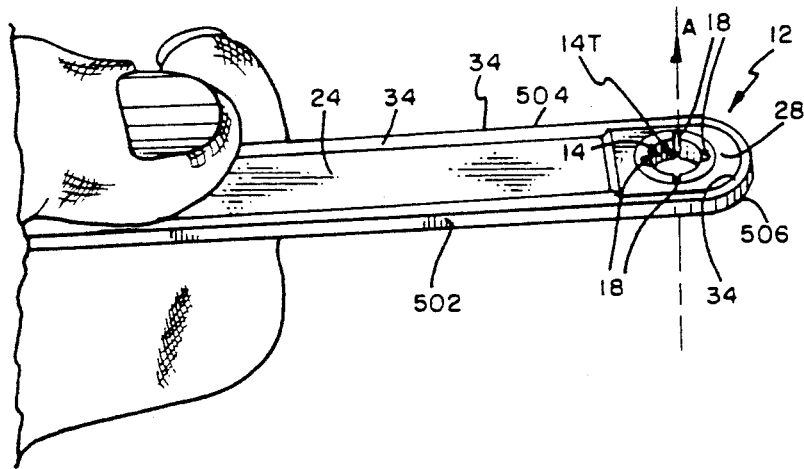
Figure 19:
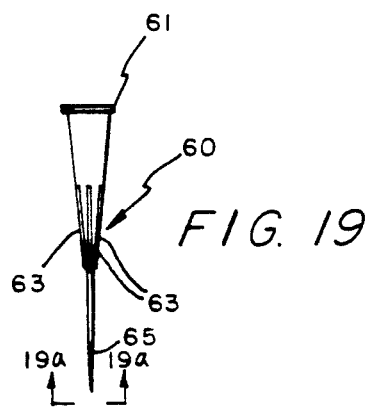
FIG. 19 is a horizontal plan view taken in direction of the arrows and along the plane of line 19—19 in FIG. 18.
Figure 20:
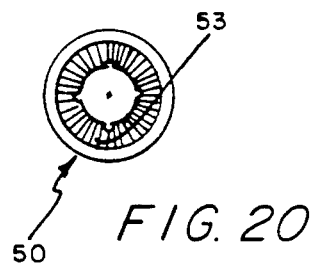
FIG. 20 is a horizontal plan view taken in direction of the arrows and along the plane of line 20—20 in FIG. 18.
Figure 19A:
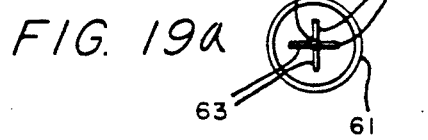
FIG. 19a is a bottom plan view taken in the direction of arrows and along the plane 19a—19a in FIG. 19.
Figure 22:
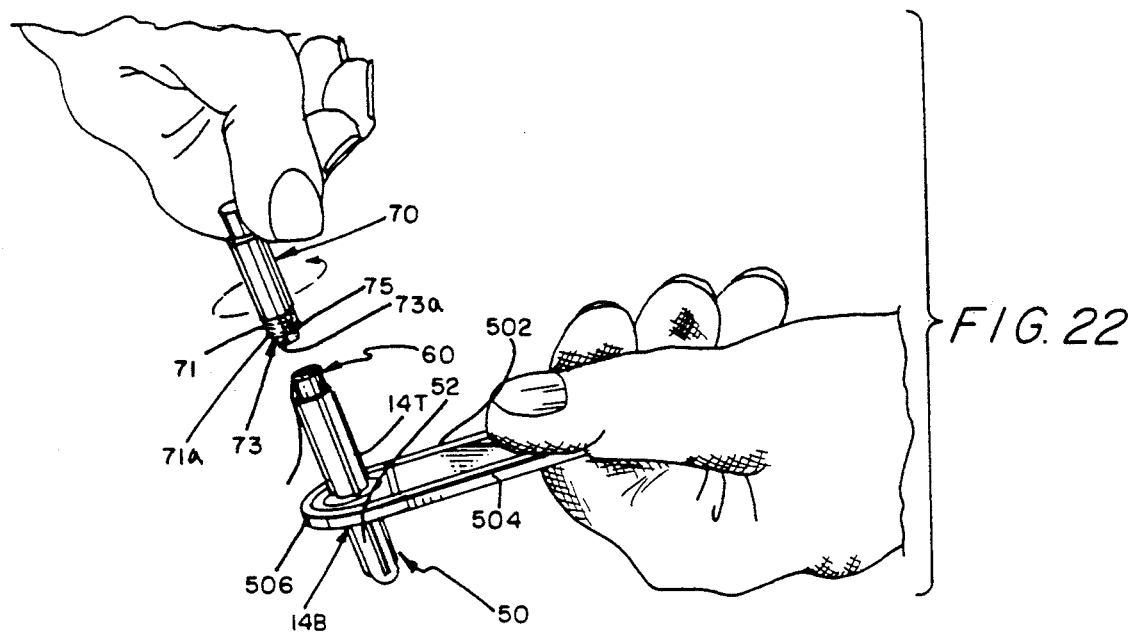
FIG. 22 is a perspective view of the wrench disengaging the combined needle cap and contaminated needle assembly from a syringe by threadably disengaging the contaminated needle assembly from the syringe.
Figure 21:
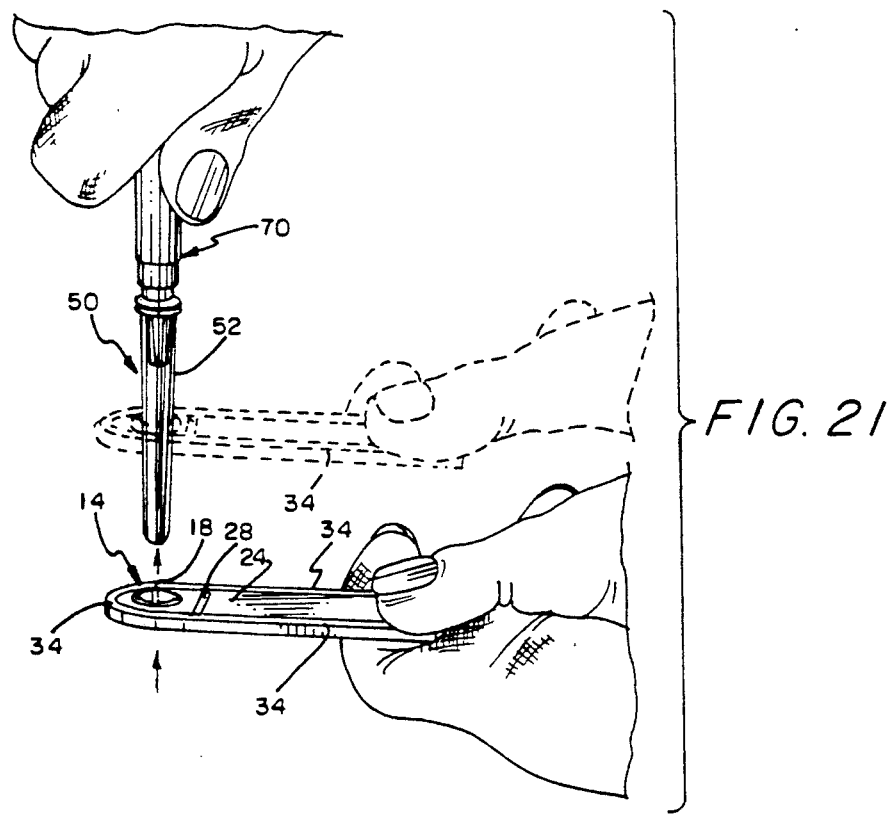
FIG. 21 is a perspective view of the combined needle cap and contaminated needle assembly secured to a syringe in the process of being engaged to the wrench, with the dotted line representation of the wrench being the wrench engaged to the needle cap which is slidably engaged to the needle assembly.

The needle cap 50 has a generally longitudinal hollow cup-like structure having at least one external rib 52 for being slidably disposed in the at least one arcuate (or semi-circular) channel 18. Preferably, there are four (4) ribs 52-52-52-52 which frictionally and slidably pass into the four (4) arcuate channels 18-18-18-18 within the cylindrical opening 14 of the tool or needle cap wrench 10 (see FIG. 6). The needle cap 50 has a fluted inside wall, generally illustrated as 51 (see FIG. 18) and having a structure defining a plurality of longitudinal channels 53. The needle assembly 60 comprises a protruding perimetrical top ridge (or lap) 61, a plurality of tapering ridges (or fins) 63, and a needle 65 secured thereto. The ridges 63 slidably pass into the channels 53 of the fluted inside wall 51 of the needle cap 50 for slidably engaging the needle assembly 60 to the needle cap 50. Such engagement permits the needle cap 50 to turn the needle assembly 60 without slippage (when the needle cap 50 is turned by the wrench 12). The syringe 70 has a lower cylindrical wall 71 with a generally smooth outer surface 71a and including an inside recess (or cavity), generally illustrated as 73, having a concentric hollow protruding cylindrical member 73a wherethrough fluids pass from the syringe 70 into the needle assembly 60; and threads 75 (see dotted lines in FIG. 22) that threadably engage to the ridge or lip 61 of the needle assembly 60 such that the needle assembly 60 may be removably engaged to the syringe 70 by passing the cylindrical member 73a into the needle assembly 60 and contacting and rotating the ridge 61 against the threads 75 for rotatably, threadably securing the needle assembly 60 to the syringe 70.

With continuing reference to the drawings for operation of the invention, needle cap wrench 10 is designed to provide dental, laboratory, veterinary and health care workers with a tool by which they could, during utilization of injection devices (such as syringe 70) having removable needle covers or caps 50 or sabots or the like, safely remove such covers 50, caps, or sabots, and replace or recap such used or contaminated needles (such as needle assembly 60) with greatly reduced risk of injury, i.e. needle stick, by the contaminated needle. The tool or wrench 10 of this invention is also designed to provide a means by which the worker could remove the needle cap 50 and needle assembly 60 from the syringe 70 and eject the same into the container or receptacle 100 designated to receive such sharp instruments after use or contamination. The needle cap wrench 10 is also created to provide a means by which the health care worker and his or her employer could comply with the OSHA regulatory requirement that demands such recapping or needle removal must be accomplished through the use of a mechanical device or a one handed technique.

Figure 8:
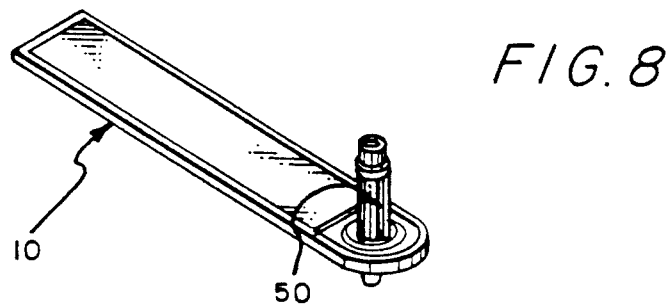
FIG. 8 is a perspective view of the wrench engaged to the needle cap and disposed in an upright position.
Figure 12:
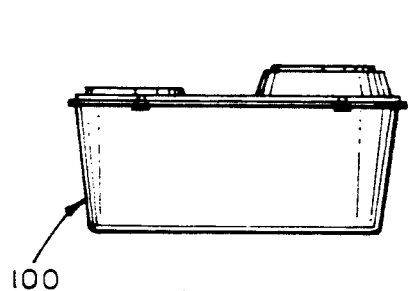
FIG. 12 is partial front elevational view of a container for receiving a contaminated needle and needle cap combination.
Figure 11:
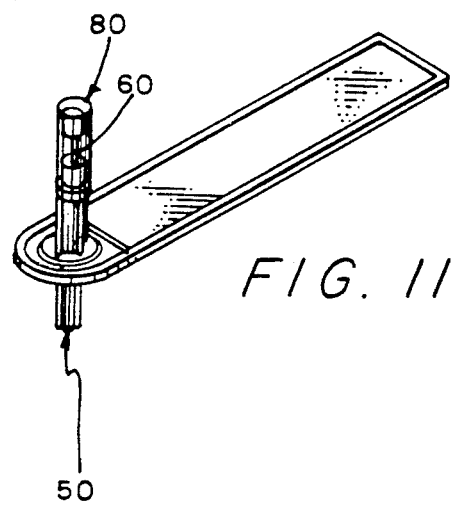
FIG. 11 is a perspective view of the tool or wrench engaged therewith and encapsulating a needle assembly which was removed from a syringe.
Figure 9:
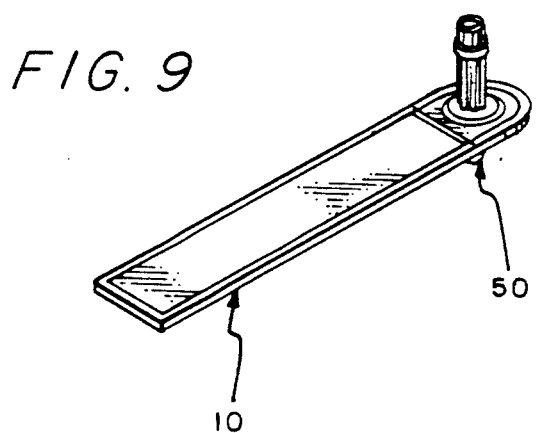
FIG. 9 is a another perspective view of the wrench engaged to the needle cap and disposed in an upright position.
Figure 10:
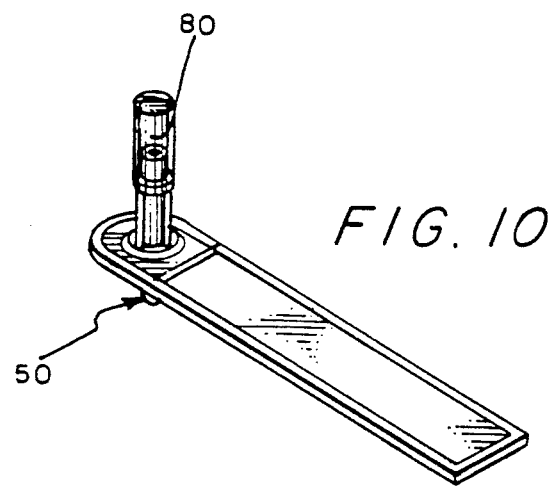
FIG. 10 is a perspective view of the tool or wrench engaged to the needle cap and disposed in an upright position with a cover removably engaged to the needle cap.

The needle cap wrench 10 is to be installed on the needle cap 50 when the syringe 70 or injection device is to be used or sometime prior to use. It is retained on the cap 50 by friction and the ribbed structure (i.e. ribs 52) of the needle cap 50 frictionally passing through the arcuate channels 18. Immediately prior to the injection procedure the needle cap 50 is removed from the needle assembly 60 or syringe needle assembly using the needle cap wrench 10 as a handle. Once the injection procedure is complete the needle cap 50, still installed in the needle cap wrench 10, may then be replaced over the now contaminated needle 60 or syringe/needle assembly. In addition, the needle cap wrench 10, with the needle cap 50 in place, is designed to set upright (as best shown in FIGS. 8 and 9) to permit reinsertion of the needle 60 with a one handed technique if desired by the operator. Once the needle assembly 60 is properly recapped the needle cap wrench 10 may then be used as handle to unscrew or detach the entire contaminated needle assembly 60 from the syringe 70 for ejection into a suitable container or receptacle 100, all as previously described above. Ejection is accomplished by thumb or finger pressure on the blunt or closed end of the needle cap or sabot 50 (see FIG. 17), the needle cap wrench 10 may now be cleaned, disinfected, and chemically or heat sterilized for reuse.

Figure 13:
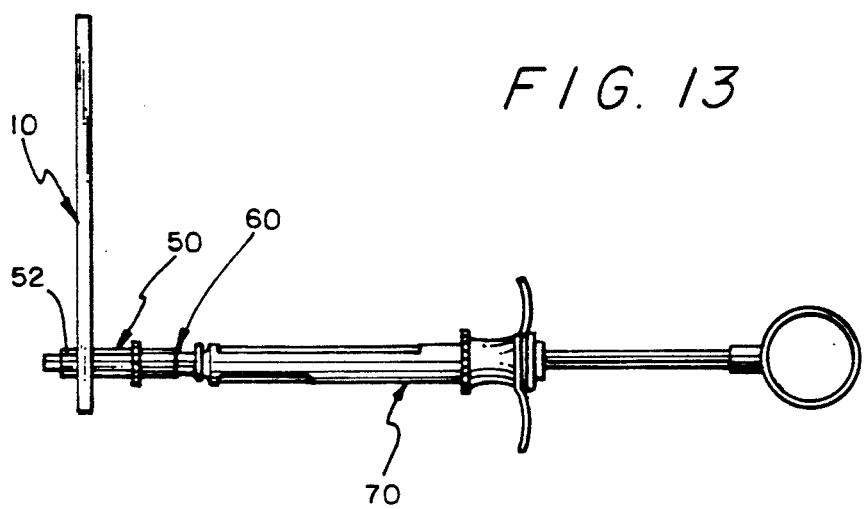
FIG. 13 is a side elevational view of the wrench engaged to a needle cap which is removably secured to a needle assembly releasably engaged to a syringe.
Figure 14:
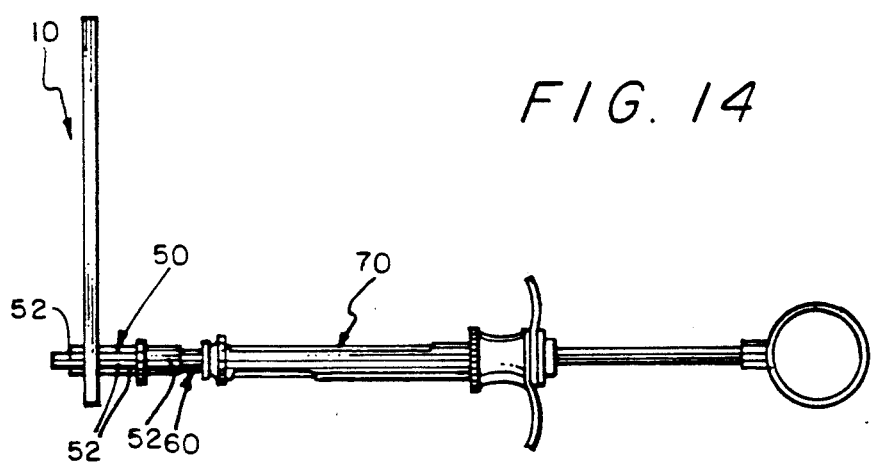
FIG. 14 is another side elevational view of the wrench engaged to a needle cap which is removably secured to a needle assembly releasably engaged to a syringe.
Figure 15:
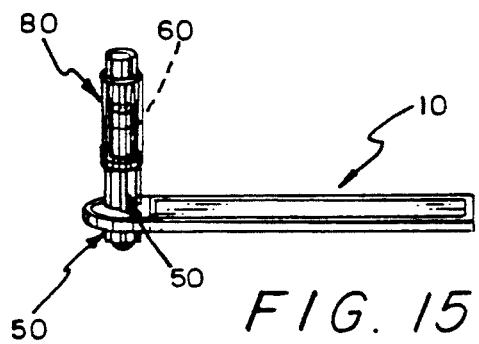
FIG. 15 is a perspective view of the wrench engaged to a needle cap and with the wrench tilted on its side against a horizontal plane and with a cover releasably engaged to the needle cap and having a contaminated needle encapsulated therein.
Figure 16:
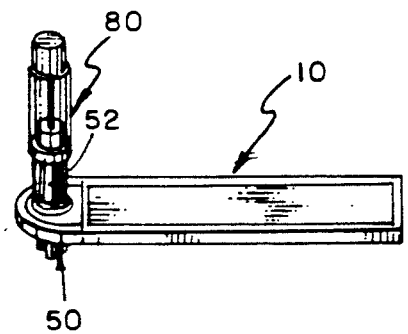
FIG. 16 is a part perspective view of the assembly of FIG. 15 in a non-tilted position or generally upright position.

The needle cap wrench 10 is a flat bar of material that is square on one or both ends with a hole (or holes) or opening (openings) 14 at one or both ends. Such holes or openings 14 are fluted or grooved with arcuate channels 18 as may be necessary to accommodate the needle cap 50 design or configuration. Such holes or openings preferably are designed to accommodate precisely and exactly the needle ca design or configuration of any particular needle or needle cap manufacturer. The needle cap wrench 10 is customized according to the needle cap product or assembly it is to accommodate. This is done using an interchangeable aperture insert, matching the desired configuration or design of the needle cap or assembly, in the tooling or die or mold used to manufacture the wrench. The wrench 10 is flat or square on at least one end to permit the device to rest upright when a needle cap 50 or sabot is in place in the accommodating opening or hole as best shown in FIGS. 8-11 and 16. This is to permit reinsertion or recapping of the needle assembly 60 by a one handed technique if desired. Such one handed technique comprises inserting the needle assembly 60 (when attached to the syringe 70) into the combined cap 50/wrench 10 assembly when the latter is in the posture of FIGS. 8 and 9; and subsequently the entire combination may be tilted over to the positions depicted in FIGS. 13 and 14. This feature may be eliminated by specification if so desired by the end user and a tool rounded at both ends may be fabricated.

Figure 23:
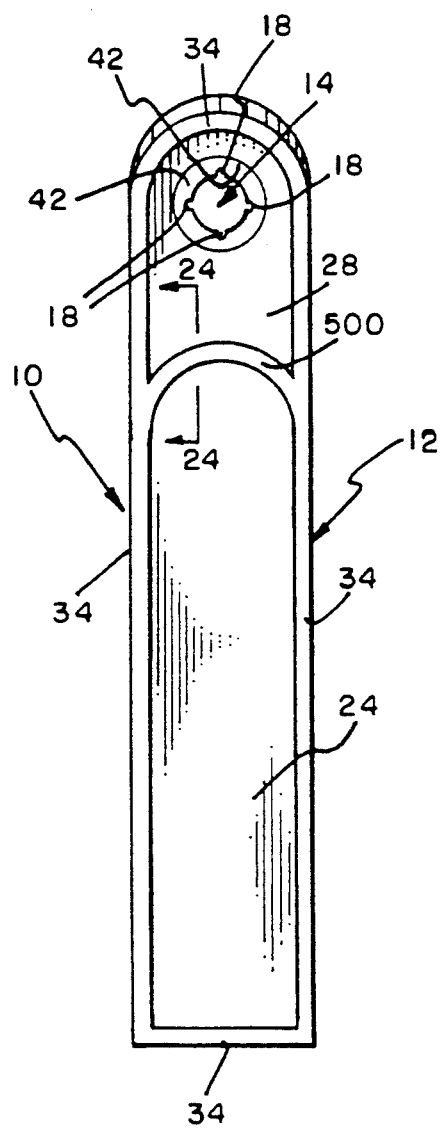
Figure 24:
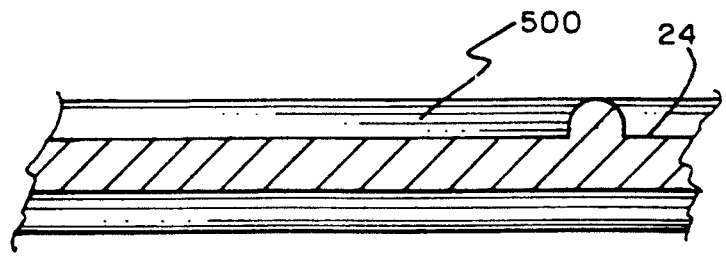

The needle cap wrench 10 is designed to be a flat bar of material preferably about five (5) inches in length and one (1) inch wide and one quarter ($\frac{1}{4}$) inch thick. These dimensions may vary as specification requirements, application, and function may dictate. The needle cap wrench 10 is designed to be constructed of a variety of material including but not limited to: polystyrene (all densities), ABS plastic, high temperature thermoplastic, polysulfone, nylon, filled nylon, filled composites, lexan, plexiglass or methyl methacrylates, base metals, aluminum and aluminum alloys, stainless steel, and other materials as function, circumstances, and consumer or regulatory demand may require. As best shown in FIGS. 23 and 24, the needle cap wrench 10 may include a thumb stop 500 or rest on one or both sides. As shown by FIG. 23, the thumb stop 500 or rest is bound to the recess 24, and is also preferably bound to both sides of the perimetrical ridge 34.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A tool for removing and replacing a needle cap from a combined needle cap and needle assembly comprising a generally longitudinal wrench structure means for removing and replacing a needle cap from a needle assembly; said longitudinal wrench structure means defining a generally cylindrical opening having an opening axis that is perpendicular to the longitudinal wrench structure means, and further having an open top, an open bottom, and a cylindrical wall with at least one arcuate channel traversing said cylindrical wall; a distance between one of said first opposed arcuate channels and one of said second opposed arcuate channels is defined by an approximately 90 degrees arc; said generally longitudinal structure means further defines a first recess and a second recess terminating in a first wrench platform and a second wrench platform respectively; and additionally comprising a first ridge integrally formed on said first wrench platform and circumscribing said generally cylindrical opening, and a second ridge integrally formed on said second wrench platform and circumscribing said generally cylindrical opening.

2. The tool of claim 1 wherein said longitudinal wrench structure means additionally defines a first continuous perimetrical ridge integrally secured to said first wrench platform and forming boundaries for said first recess, and a second continuous perimetrical ridge integrally secured to said second wrench platform and forming boundaries for said second recess.

3. The tool of claim 2 additionally comprising said needle cap slidably engaged to said generally longitudinal wrench structure means through said generally cylindrical opening, such that said needle cap passes through said open top and said open bottom of said generally cylindrical opening, said needle cap having a structure generally defining a longitudinal hollow cap-like structure having four external ribs slidably disposed in said pair of said first opposed arcuate channels and in said pair of second opposed arcuate channels.

4. The tool of claim 1 wherein said longitudinal wrench structure means additionally defines a first continuous perimetrical ridge integrally secured to said first wrench platform and forming boundaries for said first recess, and a second continuous perimetrical ridge integrally secured to said second wrench platform and forming boundaries for said second recess.

5. The tool of claim 4 additionally comprising a needle cap slidably engaged to said generally longitudinal wrench structure means through said generally cylindrical opening, such that said needle cap passes through said open top and said open bottom of said generally cylindrical opening, said needle cap having a cup-like structure generally defining a longitudinal hollow cup-like structure having four external ribs slidably disposed in said pair of first opposed arcuate channels and in said pair of second opposed arcuate channels.

6. The tool of claim 5 additionally comprising a hypodermic needle slidably disposed in said needle cap, and a generally hollow top slidably engaged to the needle cap for encapsulating the hypodermic needle within said needle cap.

7. The tool of claim 1 additionally comprising said needle cap slidably engaged to said generally longitudinal wrench structure means through said generally cylindrical opening, such that said needle cap passes through said open top and said open bottom of said generally cylindrical opening, said needle cap having a structure generally defining a longitudinal hollow cup-like structure having at least one external rib slidably disposed in said at least on arcuate channel.

8. A tool for removing and replacing a needle cap from a combined needle cap and needle assembly comprising a generally longitudinal wrench structure defining a generally cylindrical opening having a cylindrical wall with at least one arcuate channel traversing said cylindrical wall; said cylindrical wall has a pair of first opposed arcuate channels traversing said cylindrical wall, and a pair of second opposed arcuate channels and wherein said longitudinal wrench structure means additionally comprises a pair of opposed parallel ends having an equal length, a first arcuate end, and a second end generally perpendicular to said parallel ends and having a length less than said equal length of said parallel sides; wherein said first and second arcuate channels are generally equispaced from each other along said cylindrical wall; said generally longitudinal structure means further defines a first recess and a second recess terminating in a first wrench platform and a second wrench platform respectively; and comprising a first ridge integrally formed on said first wrench platform and circumscribing said generally cylindrical opening, and a second ridge integrally formed on said second wrench platform and circumscribing said generally cylindrical opening.

* * * * *